United States Patent
Rock

(10) Patent No.: US 9,582,641 B2
(45) Date of Patent: Feb. 28, 2017

(54) DISTRIBUTED HEALTHCARE DATABASE SYSTEM AND METHOD

(71) Applicant: Eric Rock, Plano, TX (US)

(72) Inventor: Eric Rock, Plano, TX (US)

(*) Notice: Subject to any disclaimer, the term of this patent is extended or adjusted under 35 U.S.C. 154(b) by 0 days.

(21) Appl. No.: 14/224,762

(22) Filed: Mar. 25, 2014

(65) Prior Publication Data

US 2014/0297330 A1    Oct. 2, 2014

Related U.S. Application Data

(63) Continuation-in-part of application No. 14/224,666, filed on Mar. 25, 2014, and a continuation-in-part of application No. 14/223,747, filed on Mar. 24, 2014, and a continuation-in-part of application No. 14/223,652, filed on Mar. 24, 2014, and a continuation-in-part of application No. 14/223,537, filed on Mar. 24, 2014, and a continuation-in-part of application No. 14/223,815, filed on Mar. 24, 2014.

(60) Provisional application No. 61/805,355, filed on Mar. 26, 2013.

(51) Int. Cl.
G06F 19/00 (2011.01)

(52) U.S. Cl.
CPC .................. *G06F 19/322* (2013.01)

(58) Field of Classification Search
CPC . G06F 17/3056; G06F 19/3456; G06F 19/322
USPC .......................................................... 705/3
See application file for complete search history.

(56) References Cited

U.S. PATENT DOCUMENTS

| | | | |
|---|---|---|---|
| 7,739,126 B1 | 6/2010 | Cave et al. |
| 8,183,998 B2 | 5/2012 | Rao et al. |
| 8,301,233 B2 | 10/2012 | Zhang et al. |
| 8,321,808 B2 | 11/2012 | Goetz et al. |

(Continued)

FOREIGN PATENT DOCUMENTS

WO    WO 2013033655 A1    3/2013

OTHER PUBLICATIONS

Doukas, et. al., "Mobile Healthcare Information management Utilizing Cloud Computing and Android OS"; 32nd Annual International Conference of the IEEE EMBS Buenos Aires, Argentina, Aug. 31-Sep. 4, 2010.

*Primary Examiner* — Hiep V Nguyen
(74) *Attorney, Agent, or Firm* — David W. Carstens; Krista Y. Chan; Carstens & Cahoon, LLP

(57) ABSTRACT

A system and method distributing healthcare database access is disclosed. The system and method interpose a data mapping server (DMS) between a data request user server (DRS) and data service user server (DSS) to manage data transfers between the DSS and the DRS such that disparate database characteristics of the DRS/DSS are accommodated in real-time and permit asynchronous healthcare activity to be triggered. The DMS operates with a data access matrix (DAM) having each referenced DRS/DSS intersection pair associated with read/write control processes (RWP) that include read data (RDD) and write data (WRD) processes to permit data access across the disparate DRS/DSS database boundaries. The DAM may have multiple dimensions to accommodate asynchronously activated process threads within an overall patient healthcare plan (PHP) that operate to trigger healthcare provider alarms and other activity associated with the transfer/update of data between the DSS and the DRS.

15 Claims, 8 Drawing Sheets

(56) References Cited

U.S. PATENT DOCUMENTS

| | | |
|---|---|---|
| 8,326,651 B2 | 12/2012 | McLaren et al. |
| 8,396,804 B1 | 3/2013 | Dala et al. |
| 2002/0184055 A1 | 12/2002 | Naghavi et al. |
| 2006/0234202 A1 | 10/2006 | Brown |
| 2007/0006322 A1* | 1/2007 | Karimzadeh et al. .......... 726/27 |
| 2007/0191070 A1 | 8/2007 | Rao |
| 2007/0255345 A1 | 11/2007 | Krause |
| 2008/0242947 A1 | 10/2008 | Jung et al. |
| 2008/0275317 A1 | 11/2008 | Cho et al. |
| 2009/0150416 A1* | 6/2009 | Baker et al. ................. 707/100 |
| 2011/0029327 A1 | 2/2011 | Dunlop |
| 2011/0166884 A1 | 7/2011 | Lesselroth et al. |
| 2011/0234409 A1 | 9/2011 | Soliman |
| 2011/0238435 A1 | 9/2011 | Rapaport et al. |
| 2011/0295621 A1 | 12/2011 | Farooq et al. |
| 2012/0041771 A1 | 2/2012 | Cosentino et al. |
| 2013/0035955 A1 | 2/2013 | Torres |
| 2013/0329058 A1 | 12/2013 | Brossette et al. |

\* cited by examiner

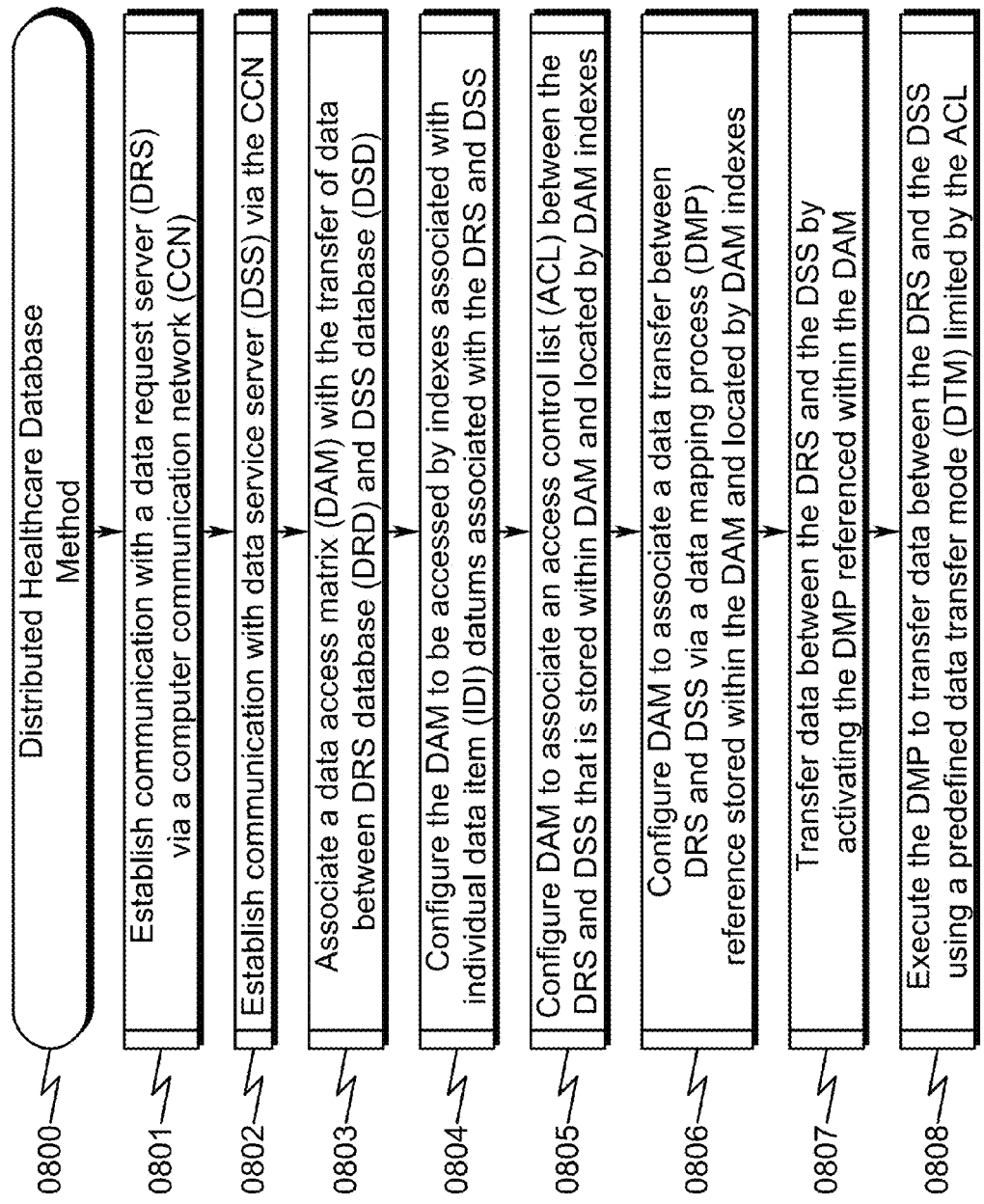

DISTRIBUTED HEALTHCARE DATABASE SYSTEM AND METHOD

CROSS REFERENCE TO RELATED APPLICATIONS

U.S. Provisional Patent Applications

This application claims benefit under 35 U.S.C. §119 and incorporates by reference United States Provisional Patent Application for HEALTHCARE MANAGEMENT SYSTEM AND METHOD by inventor Eric Rock, filed electronically with the USPTO on Mar. 26, 2013, with Ser. No. 61/805,355, EFS ID 15358332, confirmation number 6386.

U.S. Utility Patent Applications

This application claims benefit under 35 U.S.C. §120 and incorporates by reference United States Utility Patent Application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

This application claims benefit under 35 U.S.C. §120 and incorporates by reference United States Utility Patent Application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

This application claims benefit under 35 U.S.C. §120 and incorporates by reference United States Utility Patent Application for DYNAMIC VIDEO SCRIPTING SYSTEM AND METHOD by inventor Eric Rock, filed electronically with the USPTO on Mar. 25, 2014, with Ser. No. 14/223,815, EFS ID 18568932, confirmation number 2060. This patent application will be referred to herein as the DYNAMIC VIDEO SCRIPTING SYSTEM AND METHOD patent application.

This application claims benefit under 35 U.S.C. §120 and incorporates by reference United States Utility Patent Application for MEDICATION RECONCILIATION SYSTEM AND METHOD by inventor Eric Rock, filed electronically with the USPTO on Mar. 24, 2014, with Ser. No. 14/223,747, EFS ID 18568406, confirmation number 1061. This patent application will be referred to herein as the MEDICATION RECONCILIATION SYSTEM AND METHOD patent application.

This application claims benefit under 35 U.S.C. §120 and incorporates by reference United States Utility Patent Application for VIRTUAL REHABILITATION SYSTEM AND METHOD by inventor Eric Rock, filed electronically with the USPTO on Mar. 25, 2014, with Ser. No. 14/224,666, EFS ID 18577154, confirmation number 5019. This patent application will be referred to herein as the VIRTUAL REHABILITATION SYSTEM AND METHOD patent application.

U.S. Continuation-In-Part (CIP) Patent Application

This application is a continuation-in-part (CIP) patent application of and incorporates by reference United States Utility Patent Application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

This application is a continuation-in-part (CIP) patent application of and incorporates by reference United States Utility Patent Application for VIDEO DATA EXTENSION SYSTEM AND METHOD by inventor Eric Rock, filed electronically with the USPTO on Mar. 24, 2014, with Ser. No. 14/223,652, EFS ID 18567689, confirmation number 1380. This patent application will be referred to herein as the VIDEO DATA EXTENSION SYSTEM AND METHOD patent application.

This application is a continuation-in-part (CIP) patent application of and incorporates by reference United States Utility Patent Application for DYNAMIC VIDEO SCRIPTING SYSTEM AND METHOD by inventor Eric Rock, filed electronically with the USPTO on Mar. 24, 2014, with Ser. No. 14/223,815, EFS ID 18568932, confirmation number 2060. This patent application will be referred to herein as the DYNAMIC VIDEO SCRIPTING SYSTEM AND METHOD patent application.

This application is a continuation-in-part (CIP) patent application of and incorporates by reference United States Utility Patent Application for MEDICATION RECONCILIATION SYSTEM AND METHOD by inventor Eric Rock, filed electronically with the USPTO on Mar. 24, 2014, with Ser. No. 14/223,747, EFS ID 18568406, confirmation number 1061. This patent application will be referred to herein as the DYNAMIC VIDEO SCRIPTING SYSTEM AND METHOD patent application.

This application is a continuation-in-part (CIP) patent application of and incorporates by reference United States Utility Patent Application for VIRTUAL REHABILITATION SYSTEM AND METHOD by inventor Eric Rock, filed electronically with the USPTO on Mar. 25, 2014, with Ser. No. 14/224,666, EFS ID 18577154, confirmation number 5019. This patent application will be referred to herein as the DYNAMIC VIDEO SCRIPTING SYSTEM AND METHOD patent application.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods that permit cross-database data access from a variety of hardware/software platforms, and specifically to applications in which disparate hardware/software systems must coordinate database access to patient healthcare information stored in electronic medical records. Without limiting the scope of the present invention, the present invention may be advantageously applied to the following U.S. Patent Classifications: 707/796; 707/804; 705/2; 705/3; 713/193; 707/999.001; 707/999.003; and 707/999.01.

PRIOR ART AND BACKGROUND OF THE INVENTION

Prior Art System Context

Within the context of automated healthcare delivery systems there is often a need for healthcare professionals to access electronic medical records that span multiple hardware/software systems. These hardware/software systems often are spatially diverse and incorporate incompatible operating systems, data structures, and processing flows. Generally speaking, these disparate hardware/software healthcare systems transfer information between the different system using batch translation and update procedures in which modified records in a source system/database are extracted, transmitted to a target computer system, and there translated into native target database formats and integrated within the native target database. In this manner, healthcare systems having differing formats can cross-communicate information relating to patient updates to permit each system to have a complete patient history/electronic medical record.

Deficiencies in the Prior Art

The prior art as detailed above suffers from the following deficiencies:
  Prior art distributed healthcare database systems and methods do not permit real-time updating of EMR data among a variety of healthcare computer systems.
  Prior art distributed healthcare database systems and methods do not permit real-time updating of EMR data using remote patient monitoring equipment.
  Prior art distributed healthcare database systems and methods do not permit healthcare professionals to be activated in the event of critical patient medical updates.
  Prior art distributed healthcare database systems and methods do not permit data migration to occur under control of a centrally defined patient healthcare plan (PHP).
  Prior art distributed healthcare database systems and methods do not utilize patient medical readings as a basis for automated intervention of healthcare personnel to address critical patient medical needs.
  Prior art distributed healthcare database systems and methods do not integrate distributed healthcare database information with patient history information.
  Prior art distributed healthcare database systems and methods do not integrate distributed healthcare database information into the decision process of an automated autonomous patient healthcare plan (PHP).

While some of the prior art may teach some solutions to several of these problems, the core issue of disseminating patient medical information across a variety of disparate healthcare information systems in conjunction with a unified patient healthcare plan (PHP) has not been solved by the prior art.

OBJECTIVES OF THE INVENTION

Accordingly, the objectives of the present invention are (among others) to circumvent the deficiencies in the prior art and affect the following objectives in the context of a distributed healthcare database system and method:
  (1) Provide for a distributed healthcare database system and method that permits real-time updating of EMR data among a variety of healthcare computer systems.
  (2) Provide for a distributed healthcare database system and method that permits real-time updating of EMR data using remote patient monitoring equipment.
  (3) Provide for a distributed healthcare database system and method that permits healthcare professionals to be activated in the event of critical patient medical updates.
  (4) Provide for a distributed healthcare database system and method that permits data migration to occur under control of a centrally defined patient healthcare plan (PHP).
  (5) Provide for a distributed healthcare database system and method that utilizes patient medical readings as a basis for automated intervention of healthcare personnel to address critical patient medical needs.
  (6) Provide for a distributed healthcare database system and method that integrates distributed healthcare database information with patient history information.
  (7) Provide for a distributed healthcare database system and method that integrates distributed healthcare database information into the decision process of an automated autonomous patient healthcare plan (PHP).

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention covers a system and method directed to the coordination of information flow among various healthcare providers using a data access matrix (DAM) that coordinates the database updates between a data request user server (DRS) and data service user server (DSS). The DAM provides for granular access to individual data items (IDI) provided from a variety of DSS sources and permits the data providers to control the access to these IDI on a per-DRS basis. Each IDI/DRS pair is associated with DRS/DSS read/write control processes (RWP) and include read data (RDD) and write data (WRD) processes that permit data access across disparate (and typically incompatible) database boundaries. Thus, the system permits healthcare providers using different database providers (and across disparate database network boundaries) to operate in a coordinated fashion with full access control maintained by the DRS/DSS pairs.

Structurally, the present invention in some preferred system embodiments may be described as a distributed healthcare database system comprising:
  (a) data mapping server (DMS);
  (b) data access user server (DRS);

(c) data information provider server (DSS); and
(d) data access matrix (DAM);
wherein
the DMS is configured to communicate with the DRS and the DSS through a communication network;
the DAM is configured by the DMS to indicate columns corresponding to individual data items (IDI) provided by the DSS and individual rows corresponding to data access requests by the DRS;
the DMS is configured to maintain data at the intersection of the rows and the columns corresponding to access control permissions provided by the DSS for the IDI with respect to the corresponding DRS row request;
the DMS is configured to maintain data at the intersection of the rows and the columns corresponding to database access control procedures resident on the DRS;
the DMS is configured to maintain data at the intersection of the rows and the columns corresponding to database access control procedures resident on the DSS;
the DMS is configured to activate the DRS database access control procedures in response to a DRS data request and subsequently activates the DSS databases access control procedure associated with the DAM row/column associated with the DRS request; and
the DMS is configured to transfer data between the DRS database access control procedure and the DSS database access control procedure based on the DSS access control permissions provided by the DSS for the IDI.

A corresponding preferred invention method embodiment allows data to be transferred between the DRS and DSS using processes located in the DAM and executed by the DMS and/or DRS/DSS systems to form a data bridge between disparate computer systems and database architectures. In conjunction with this data transfer capability the present invention method permits activation of healthcare related processes that are triggered by specific data movement among the DRS/DSS databases to allow rapid intervention of healthcare personnel in response to changing information relating to a patient medical condition or status.

BRIEF DESCRIPTION OF THE DRAWINGS

For a fuller understanding of the advantages provided by the invention, reference should be made to the following detailed description together with the accompanying drawings wherein:

FIG. 8 illustrates a flowchart depicting an exemplary distributed healthcare database method.

DESCRIPTION OF THE PRESENTLY PREFERRED EXEMPLARY EMBODIMENTS

Figure 1:
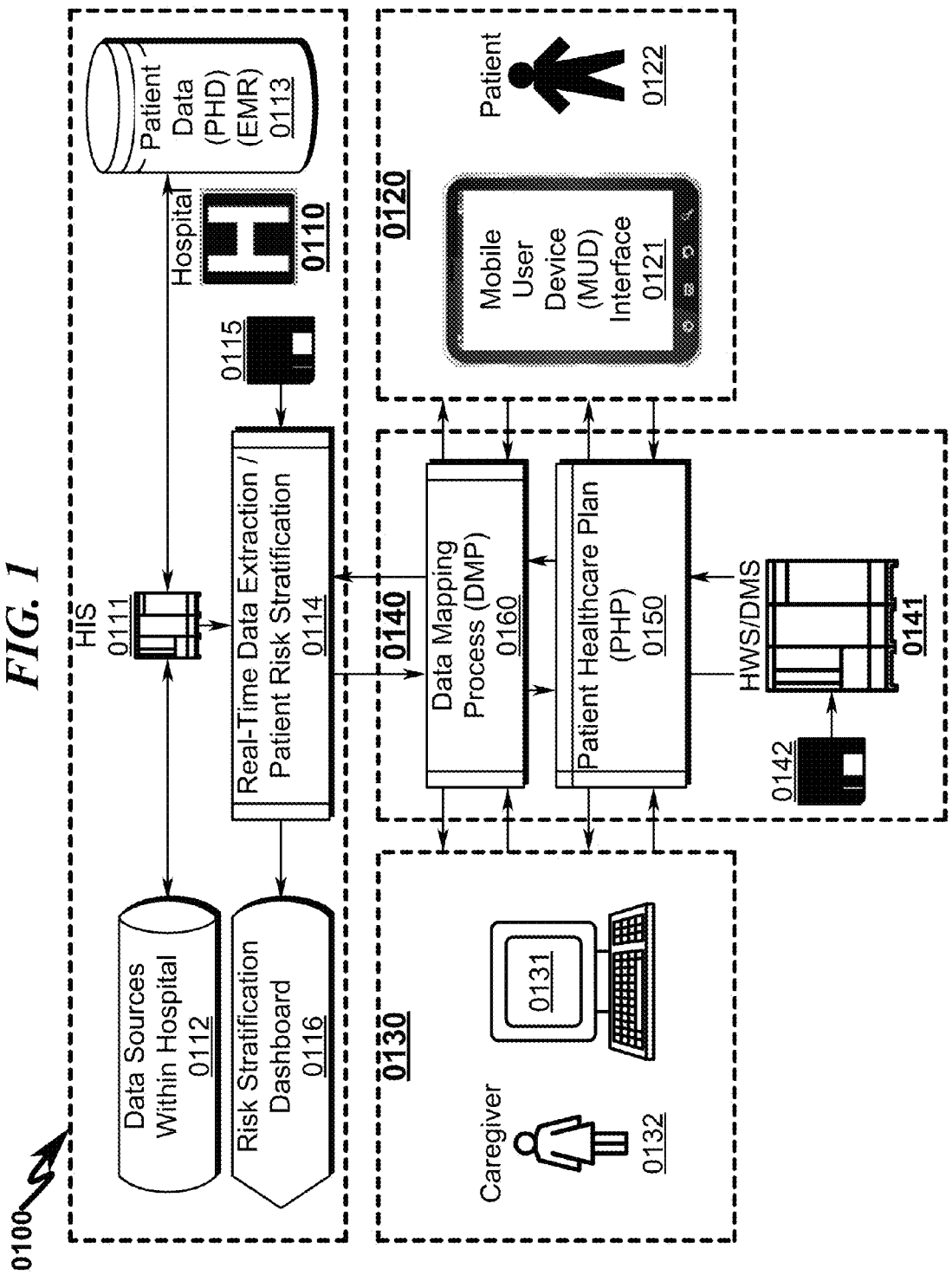
FIG. 1 illustrates an overview block diagram of a presently preferred exemplary system embodiment.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a DISTRIBUTED HEALTHCARE DATABASE SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Data Access Modes Not Limitive

The present invention anticipates a wide variety of data access modes to be supported by the distributed healthcare database system and method described herein. While read, write, and update (interlocked read/modify/write) modes are anticipated within this context, the present invention is not necessarily limited to these data access modes.

System Overview (0100)

The present invention may be summarized as depicted in the system block diagram of FIG. 1 (0100) and applied to a distributed healthcare delivery information system. In this example, a hospital (0110) incorporating a hospital information system (HIS) (0111) contains a variety of internal data sources (0112) that relate to a patient. These data sources may contain a wide variety of information relating to lab results, patient charts, procedures, etc. and may occur and be updated in real-time. This information is typically stored in a patient history database (PHD) (often referred to as an electronic medical record (EMR)) (0113). This PHD (0113) data may be used by a real-time data extraction/patient risk stratification process (0114) (as described in the HEALTHCARE DELIVERY SYSTEM AND METHOD patent application) executed from machine instructions read from a computer readable medium (0115) to provide a real-time risk stratification dashboard (0116) that enables healthcare providers to prioritize healthcare to patients that have critical medical conditions.

Traditionally, access to the PHD (0113) has been limited to healthcare professionals having direct access to the HIS (0111) system due to the disparate hardware/software used by healthcare systems outside of a particular hospital (0110) context. As each hospital (0110) or healthcare facility may have different hardware/software implemented to support their operation, the interfacing of these different systems is generally not possible. Thus, updates to patient medical information that might be obtained via a mobile user device (MUD) (0120) would not normally be incorporated within the PHD (0113), nor would information provided by a caregiver (0132) operating outside the context of the hospital (0110) setting.

The present invention addresses this problem by incorporating a data processor (0140) to act as an information interchange hub between the hospital (0110) (or other healthcare facility), a MUD (0120), and caregiver systems (0130). This data processing system (0140) comprises a computer system (0141) (also termed a host computer system (HCS) or healthcare web server (HWS) in this document) operating under control of machine instructions read from a computer readable medium (0142). The HWS (0141) allows a patient healthcare plan (PHP) (0150) to be defined to coordinate healthcare delivery to the patient among the various healthcare provider contexts (0110, 0120, 0130). This PHP (0150) is synchronized with the MUD (0120) context to allow the MUD (0121) to operate asynchronously of the other systems in the diagram.

Execution of the PHP (0150) in the MUD context (0120) or the caregiver context (0130) may result in patient information that must be integrated into the PHD (0113) in one or more hospital (0110) or healthcare facility settings. To enable this data migration, a data mapping process (DMP) (0160) is enabled in the HWS (0130) context to act as an interface between the various computer system contexts (0110, 0120, 0130). The DMP (0160) may operate under control of the HWS (0141) or in some circumstances be deployed in a separate data mapping server (DMS) specifically designed to implement the database interfacing function described herein. Within the context of the discussion of the present invention, the term data mapping server (DMS) will be used to describe the hardware system specifically designed to implement this functionality. Note in this healthcare integration context the DMS may reside as a separate component external to the hospital computer infrastructure (0110) or in some cases be incorporated within the HIS (0111) system.

System Detail (0200)

Figure 2:
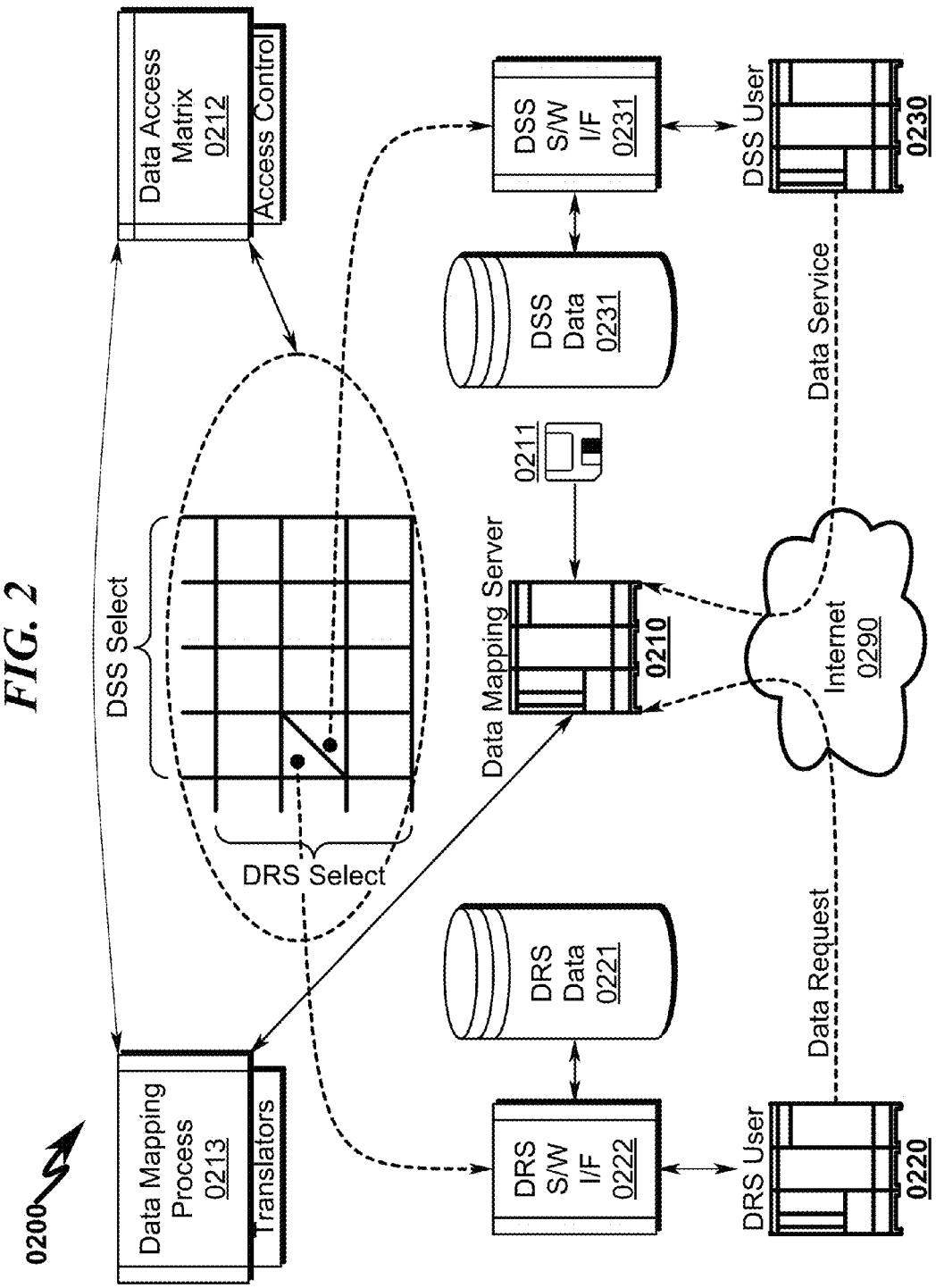
FIG. 2 illustrates a detail block diagram of a presently preferred exemplary system embodiment depicting data flows between a method and a data service user server (DSS)

Additional system detail for a preferred invention embodiment is generally illustrated in FIG. 2 (0200). In this exemplary embodiment the DMS (0210) interfaces with two generalized healthcare computer systems comprising a data request user server (DRS) (0220) and a data service user server (DSS) (0230). The DRS (0220) and DSS (0230) generically represent any two healthcare computer systems that may wish to coordinate PHD information to unify their patient healthcare views.

An exemplary data access request from the DRS (0220) to the DSS (0230) involves sending the read/write/update request from the DRS (0220) through a computer communication network (0290) (typically the Internet) to the DMS (0210). The DMS (0210) executes machine instructions read from a computer readable medium (0211) that then performs a lookup of the datum in a data access matrix (DAM) (0212). The DAM (0212) comprises a matrix relating individual data items (IDIs) in a DRS database (0221) to those contained in a corresponding DSS database (0231). A data request from the DRS (0220) to the DSS (0230) performs a row/column lookup in the DAM (0212) which retrieves access control information to validate the authority of the DRS (0220) to access the IDI within the DSS (0230). If this access validation passes, the DAM (0212) activates a data mapping process (0213) that links a DRS database interface access module (0222) with a corresponding DSS database interface access module (0232) to perform the database transfer between the DRS (0220) and the DSS (0230). The DRS/DSS database interface access modules (0222, 0232) are responsible for actual interfacing to the respective DRS/DSS databases (0221, 0231) and for proper data formatting and data translation necessary to ensure that data contained in each database (0221, 0231) is maintained in a consistent state.

Note that the DMP (0213) operating in the context of the DMS (0210) may incorporate differential encryption between each of the DRS/DSS interface modules (0222, 0232) so that the security measures associated with each of the DRS (0220) and DSS (0230) can be maintained. Thus, the system as depicted permits both data transparency between the DRS (0220) and DSS (0230) but also transparently handles differences in security protocols between the systems.

DAM Data Mapping/Healthcare Activity Processes (0300)

Figure 3:
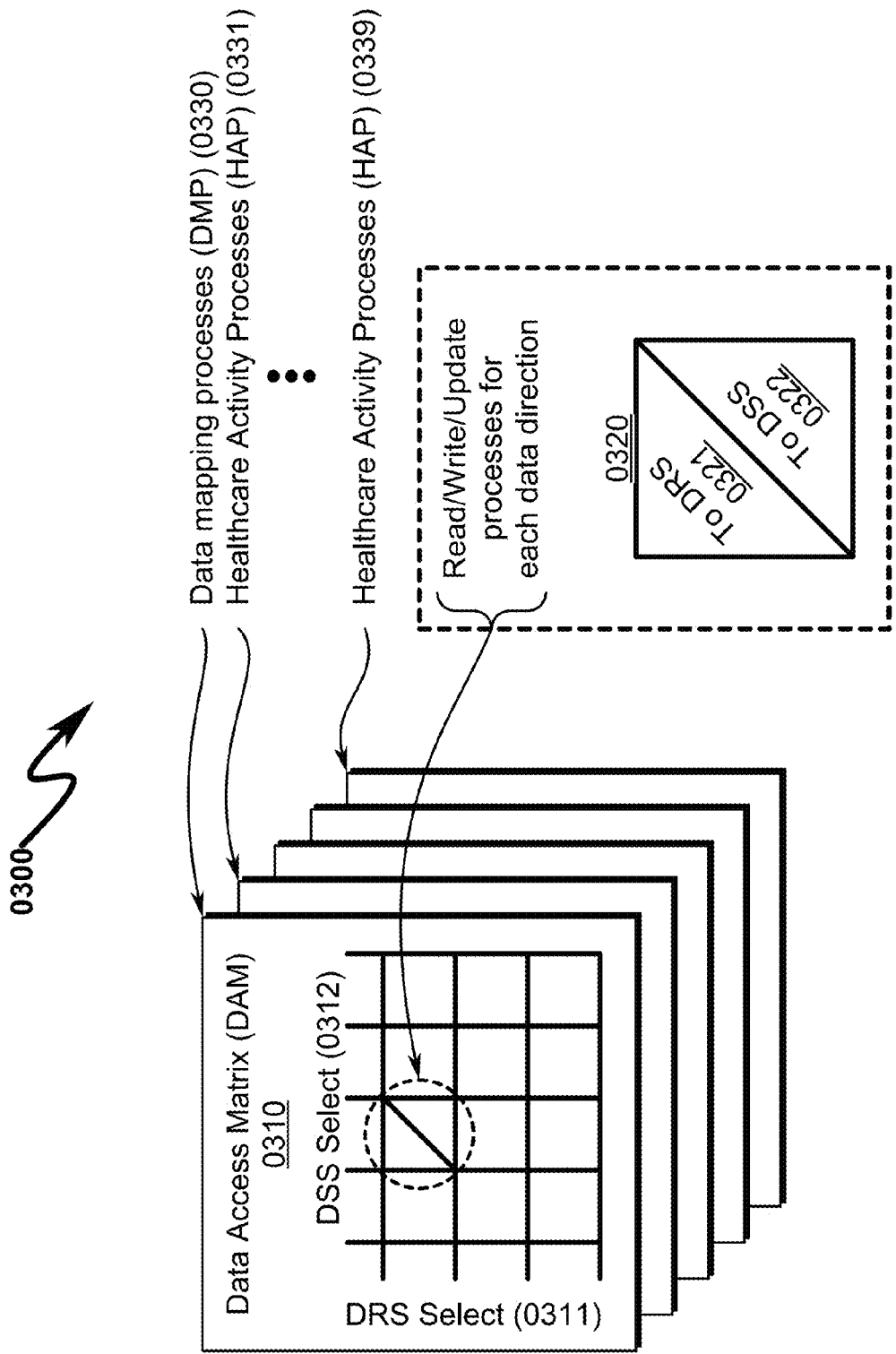
FIG. 3 illustrates an exemplary multi-dimensional data access matrix (DAM) data structure depicting both data mapping processes as well as provisions for healthcare activity mapping (HAP) processes.

A significant feature of the functionality incorporated within the data mapping server (DMS) is the ability to support both data mapping processes (DMP) as well as healthcare activity processes (HAP). As detailed in FIG. 3 (0300), the data access matrix (DAM) (0310) may be in some preferred embodiments viewed as a two-dimensional, three-dimensional, or multi-dimensional data structure. In the case of a two-dimensional structure, the DRS (0311) and DSS (0312) row/column intersection (0320) will correspond to processes that define how a read/write/update operation may be processed between the DRS/DSS in either direction (typically this will involve six processes—one for each of read/write/update in either direction (0321, 0322)).

As depicted in the diagram, the data mapping process (DMP) (0330) logical layer of the DAM may also be associated with any number of healthcare activity processes (0331, 0339) that are associated with data accesses between the DRS/DSS. This permits a data access between the DRS/DSS to trigger a healthcare activity process (HAP) that may include intervention of a healthcare professional into the healthcare delivery of the patient. Examples of this might include the following types of activity:

Triggering healthcare provider intervention when a BLOOD PRESSURE reading is logged for the patient.

Triggering healthcare provider intervention when a patient complains of CHEST PAINS in a query/response dialog as this information is logged in the patient history file.

Triggering healthcare provider intervention when medications prescribed for a patient by different physicians are contraindicated or pose a risk to the patient.

Triggering healthcare provider review of a patient history if critical patient information has not been entered or updated in the patient history file.

One skilled in the art will recognize that these HAP examples are only illustrative and not limitive of the present invention. This ability to associate HAP activity with the transfer or access of data within disparate healthcare databases permits unrelated activity associated with a particular patient to trigger healthcare provider intervention in a customized fashion for each patient.

Multiple DAM Mapping (0400)

Figure 4:
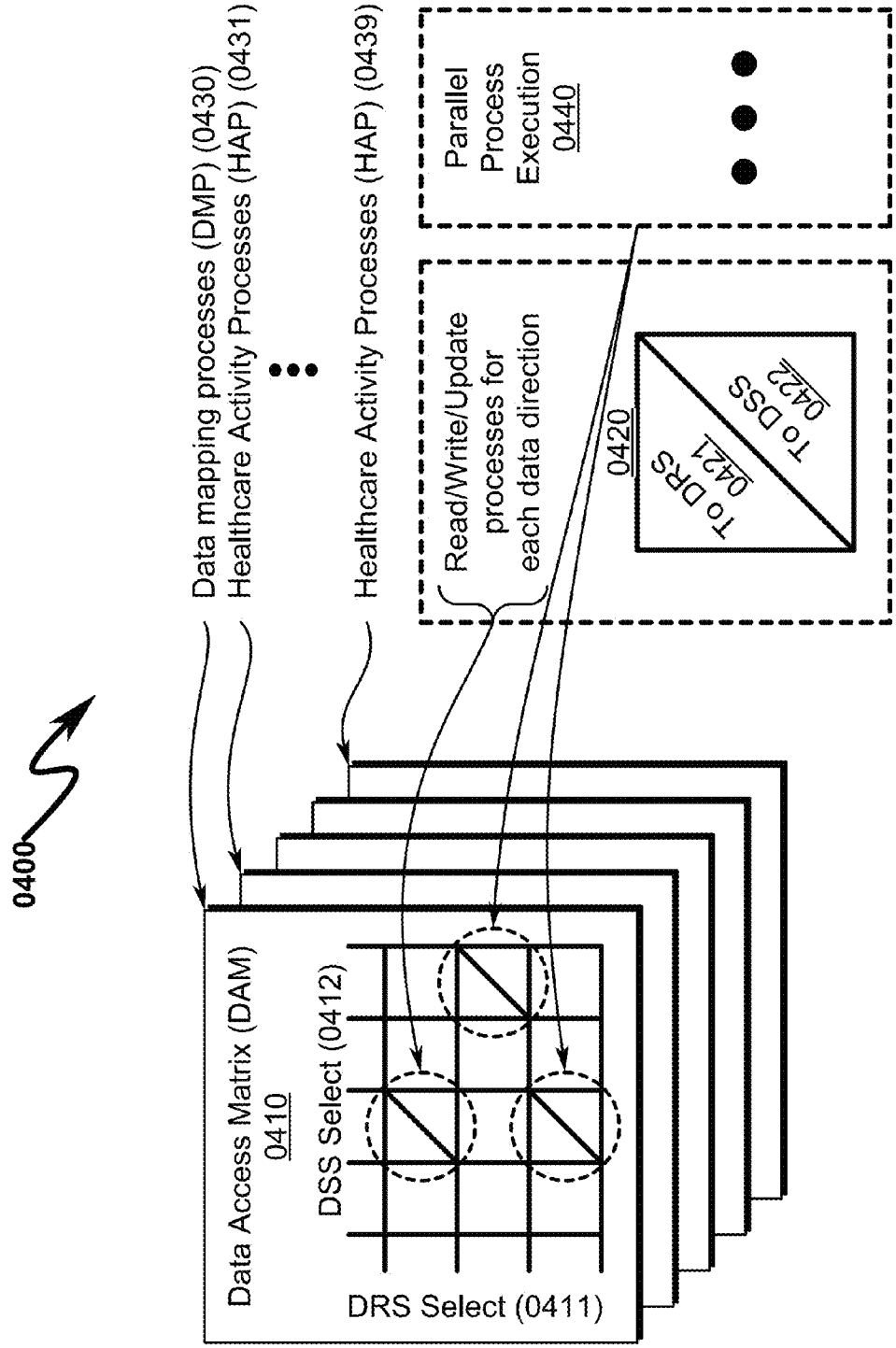
FIG. 4 illustrates an exemplary multi-dimensional data access matrix (DAM) data structure depicting both data mapping processes as well as provisions for healthcare activity mapping (HAP) processes combined with multiple DAM mapping operations.

As depicted in FIG. 4 (0400), the DAM may incorporate multiple mapping of DRS/DSS data items so that within a given database a given data item (datum) may be accessed in parallel using parallel threads (0440). There are several reasons why this type of mapping may be useful in a distributed healthcare database system:

- A datum may be replicated within one of the databases and thus require simultaneous updating when written. For example, a patient record indicating the most recent activity date and a patient record indicating the actual procedure associated with the activity. In this example, both dates should be updated simultaneously and thus two entries in the DAM (with associated access processes) are required to perform the update.
- A datum may be related to another datum in the database. For example, a patient record indicating a master list of physicians treating a patient may need to be updated to include a new physician referral or medical record update that includes a physician not previously a part of the patient history.
- A datum may require cascading of data transfers between the DRS/DSS based on data relationships between the various DAM entries. For example, updating the patient BLOOD PRESSURE reading may require triggering of healthcare provider activity that spans HEART DISEASE and DIABETES healthcare intervention. Each of these diseases may be processed by different healthcare professionals spanning the DRS/DSS boundary, and may require triggering healthcare activity or database activity that involves neither the DRS nor the DSS, as in the case of a third database that must be updated when a transfer from the DRS to the DSS occurs (here the DSS may be related to yet another database that must also be updated when the DSS is updated).

One skilled in the art will recognize that this list is illustrative and not limitive of the present invention scope.

Data Transfer Mode (DTM) Based Processing (0500)

Figure 5:
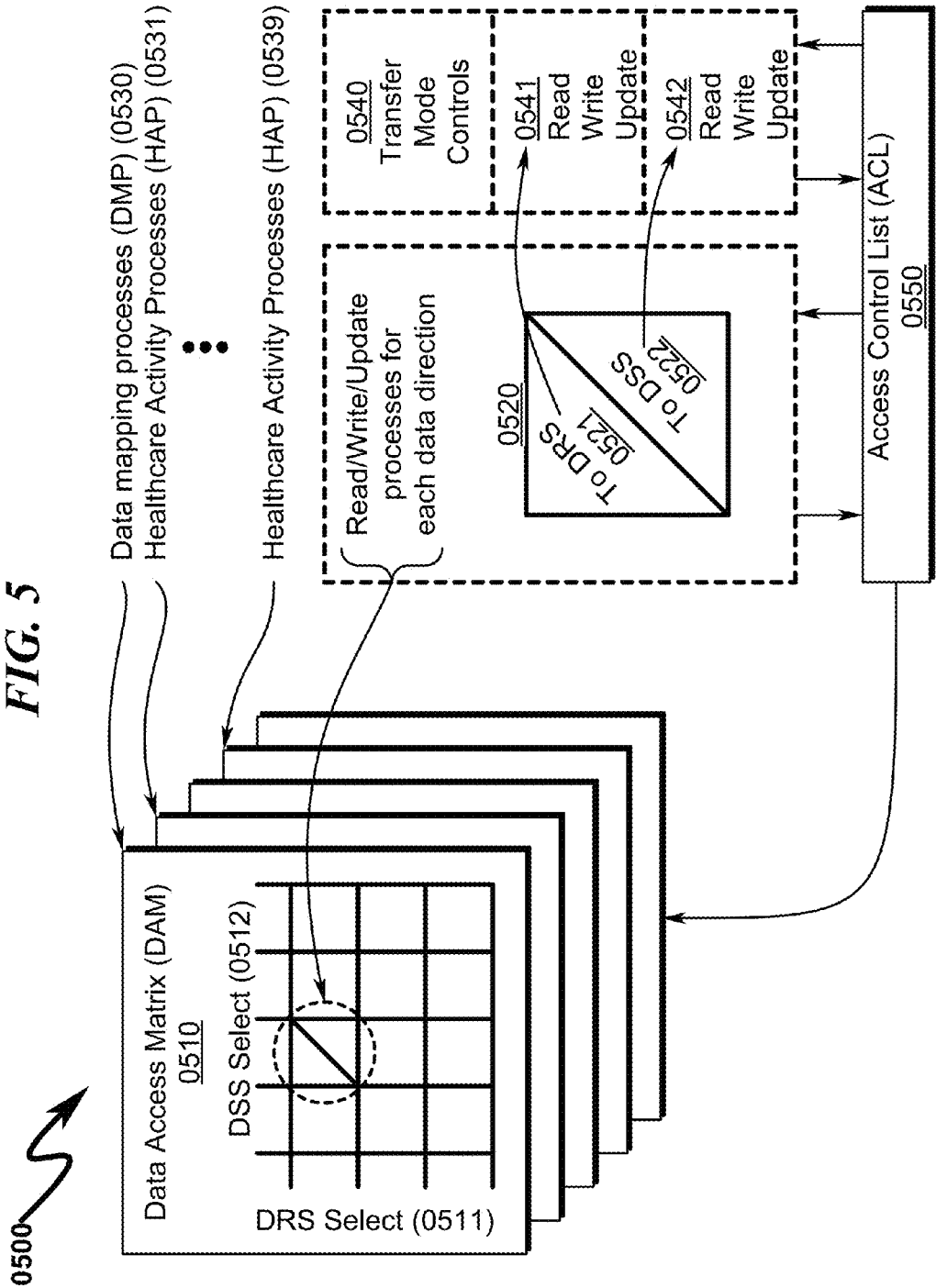
FIG. 5 illustrates an exemplary multi-dimensional data access matrix (DAM) data structure depicting both data mapping processes as well as provisions for healthcare activity mapping (HAP) processes combined with multiple DTM processing options.

The present invention anticipates that a wide variety of data transfer modes (DTM) may exist between the DRS and DSS. For example: READ, WRITE, and UPDATE (interlocked read/modify/write) operations are anticipated in a typical healthcare application context. As depicted in FIG. 5 (0500), the present invention anticipates that the data mapping process (DMP) (0520) for each DRS (0521)/DSS (0522) data transfer may have associated with them DTM-specific processes (0541, 0542) that are activated based on specific types of DTM for each DMP. For example, a special process may be activated for DRS READ access versus UPDATE access. Note that each of the database hosting systems (DRS/DSS) may have their own specific DTM-specific access processes (0541, 0542) defined in this context.

The DTM-specific processing for each of the database hosting systems (DRS/DSS) may take the form of a software process module (0541, 0542) that executes in the context of the DMS but may also be configured as a software module that is executed native to the DRS or DSS. In this alternate situation, the software process module (0541, 0542) is transferred from the DMS to either the DRS or DRS for local execution to support the specific DTM (0540) invoked by the DAM (0510) indexed entry.

Associated with each DMP there may also be an access control list (ACL) (0550) that defines the authorization of each type of data transfer mode (DTM) to occur between the DRS/DSS in each direction. Thus, a given type of transfer may be restricted based on healthcare provider privileges that are associated with the database, healthcare information system, or healthcare provider. For example, a HIS system may be authorized to READ patient information for the purposes of updating their own database records, but may be restricted to WRITE or UPDATE information in another database only in a restricted portion of the database reserved for patient information related to their practice. The DAM may incorporate a separate processing layer to provide the needed access control information necessary for the ACL (0550) to properly authorize the DTM between the DRS/DSS.

Exemplary DAM Data Structure Format (0600)-(0700)

Linked DAM Maps

Figure 6:
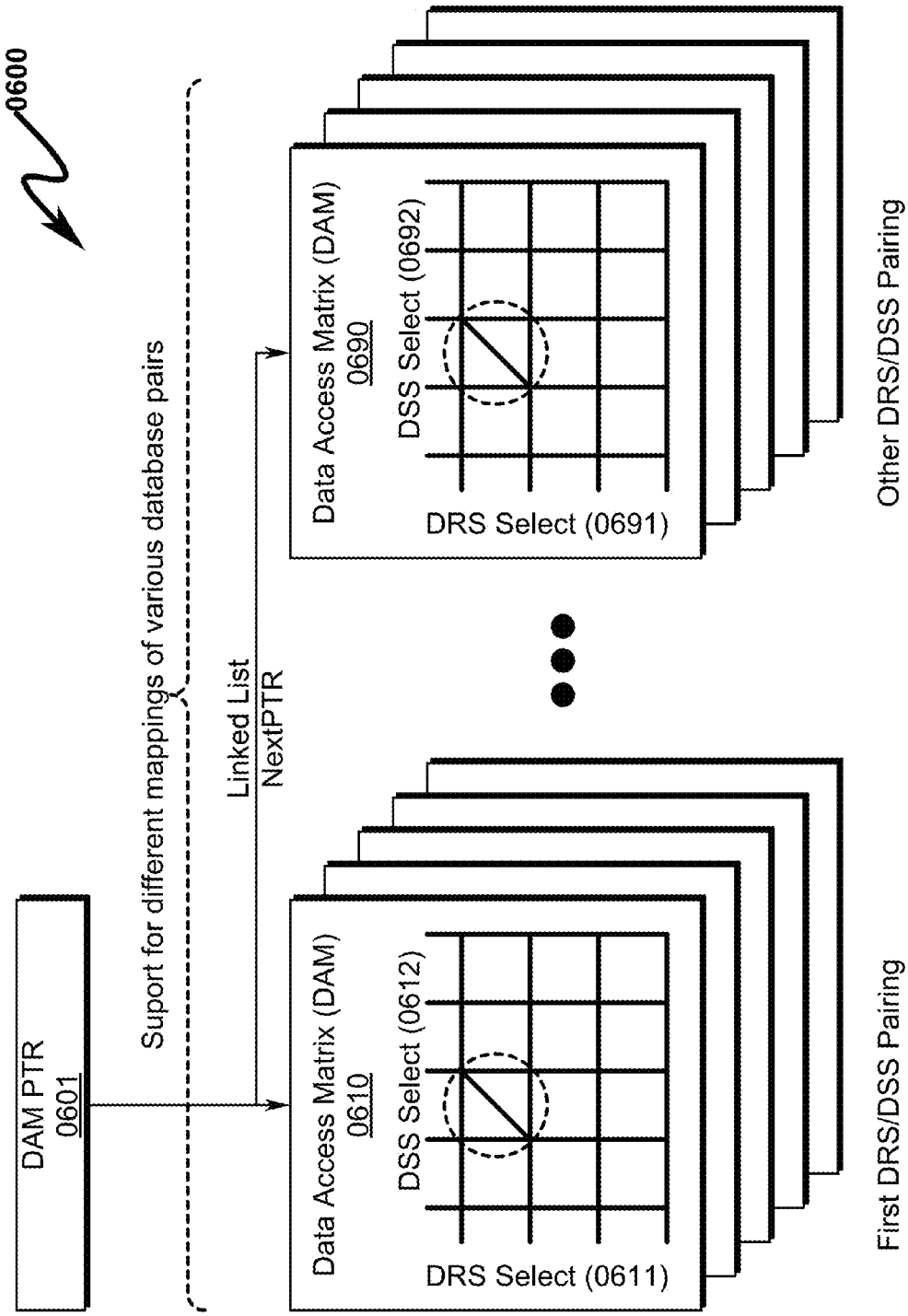
FIG. 6 illustrates an exemplary DAM data structure overview.
Figure 7:
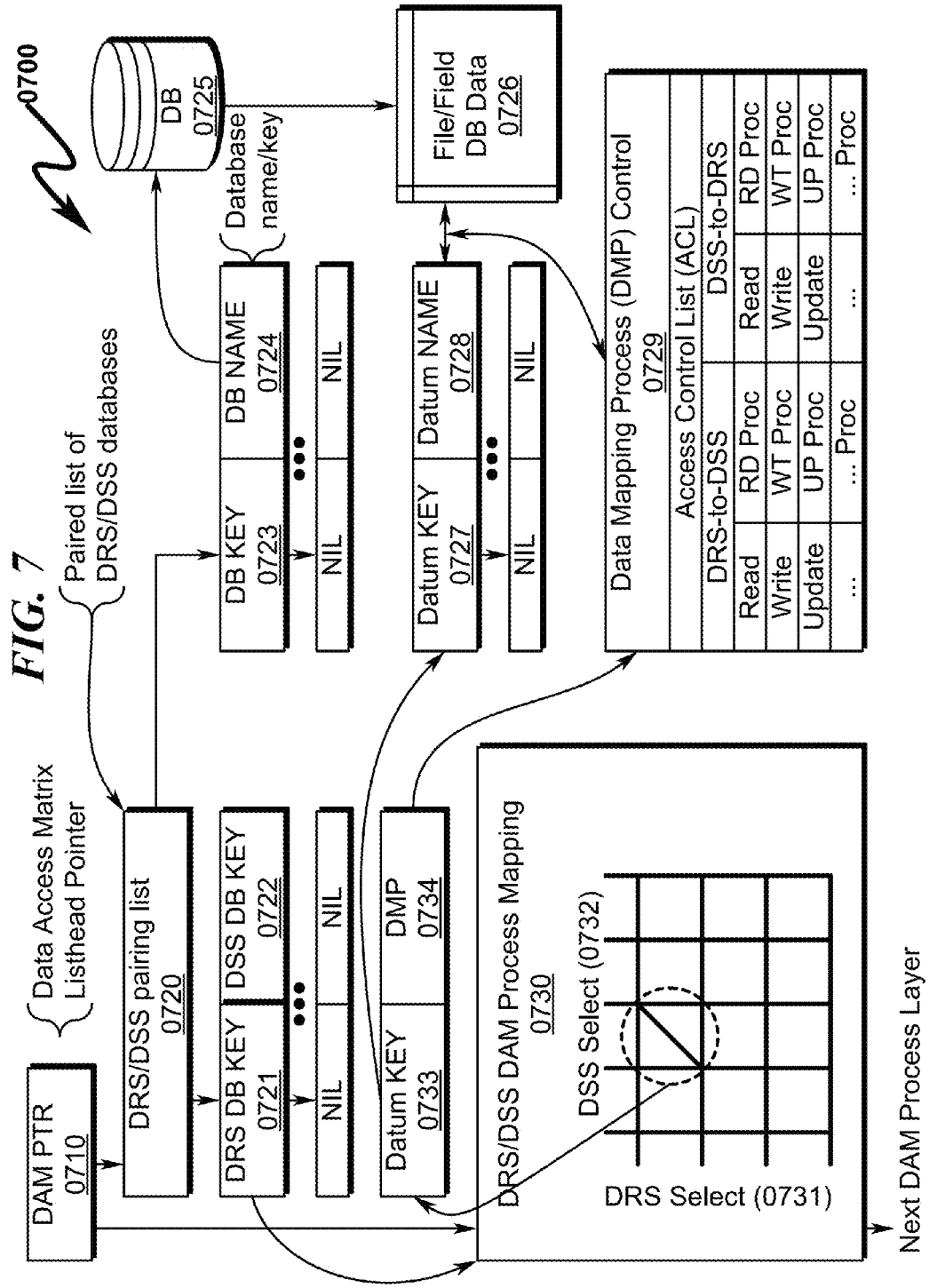
FIG. 7 illustrates an exemplary DAM data structure detail view.

While many different data structures may be utilized to implement the DAM, a preferred exemplary DAM data structure is depicted in FIG. 6 (0600) with additional detail provided in FIG. 7 (0700). These exemplary DAM data structures utilizes a DAM header pointer (0601) that links together one or more DAM mappings (0610, 0690) in a linked list. Each of the DAM mappings (0610, 0690) represents a data transfer relationship between disparate databases that may be controlled by incompatible computer systems. Each of these DAM maps (0610, 0690) may partially or fully describe the migration of data through the various incompatible computer systems as data transfers are performed.

Cascading Data Transfers

Note that this structure permits cascading data transfers to occur in situations where data modified in a first DAM (0610) relates to data contained in another DAM (0690). In this circumstance the first DAM (0610) will coordinate a database transfer. This first database transfer may then trigger another database transfer in another DAM (0690) that is either further down the linked list or in some circumstanced placed prior to the initially modified DAM database. Sequence indicators placed in each DAM can be used in these cascading updates to limit the execution of recursive or infinite loops in the cascading update process.

DAM Internal Structure

More detail of an exemplary DAM data structure is provided in FIG. 7 (0700) wherein the DAM linked list pointer (0710) links to a pairing list of DRS/DSS pairs (0720) and a linked list of DAM process mapping layers (0730). The DRS/DSS pairing list (0720) generally controls the association of database keys (0721, 0722) with the DRS/DSS data referenced in the process maps (0730) and allows a shorthand representation of the transfers to be depicted in the data transformation maps (0730). Each process layer (0730) in the DAM mapping system may represent a data translation/transform/movement from one disparate database to another and/or may include HAP processing associated with the database activity. While only one DAM process map (0730) is illustrated in this example, a plethora of individual process maps may be included in this chain and may be configured to operate synchronously (layer to layer) or asynchronously (layers simultaneously processed).

The DRS/DSS pairing list (0720) references database keys (0723) that are linked to database names (0724) referencing a specific database (0725) for DRS/DSS activity. Each of these referenced databases (0725) may have associated with it file/field references (0726) that are identified by datum key (0727) and associated datum name (0728).

The datum keys may be referenced within the DAM process map (0730) as a data pair (0733, 0734) indicating which data is associated with which DMP control structure (0729). The data mapping process (DMP) control structure (0729) dictates access control list (ACL) restrictions on the database file/field data (0726) and determines based on the data transfer direction (DRS-to-DSS or DSS-to-DRS) what data transfer mode (DTM) processes to utilize to affect the data transfer operation. These individual DTM processes may also incorporate necessary formatting changes to the data to ensure consistency of data across the data platforms (as in the case of date formats (i.e. MM/DD/YYYY vs DD/MM/YYYY) and similar data transforms that may be required).

Method Overview (0800)

The system context as depicted in FIG. 1 (0100) and FIG. 2 (0200) is typically associated with a methodology as depicted in FIG. 8 (0800) and involves the following steps:
(1) with a data mapping server (DMS), establishing communication with a data request server (DRS) via a computer communication network (CCN) (0801);
(2) with the DMS, establishing communication with a data service server (DSS) via the CCN (0802);
(3) with the DMS, associating a data access matrix (DAM) with the transfer of data between a database (DRD) controlled by the DRS and a database (DSD) controlled by the DSS (0803);
(4) with the DMS, configuring the DAM to be accessed by indexes associated with individual data item (IDI) datums associated with the DRS and the DSS (0804);
(5) with the DMS, configuring the DAM to associate an access control list (ACL) between the DRS and the DSS that is stored within the DAM and located by the DAM indexes (0805);
(6) with the DMS, configuring the DAM to associate a data transfer between the DRS and the DSS via a data mapping process (DMP) reference stored within the DAM and located by the DAM indexes (0806);
(7) with the DMS, transferring data between the DRS and the DSS by activating the DMP referenced within the DAM (0807); and
(8) with the DMS, executing the DMP to transfer data between the DRS and the DSS using a predefined data transfer mode (DTM) limited by the ACL (0808).

Note that data transferred between the DRS and DSS may be collected and updated in real-time from a medical instrumentation device (MID) communicating with a mobile user device (MUD).

Modifications to this basic methodology may include looping from step (8) to step (1) to allow the data access between the DRS and DSS to trigger another data transfer associated with other databases that are not directly controlled by the DRS/DSS servers. This cascading data transfer may span a plethora of healthcare databases and permits one data transfer to propagate through a system of interconnected datasets to allow these disparate datasets to become coherent without the need for individual computer systems controlling these datasets to directly cooperate with each other.

Patient Healthcare Plan (PHP) Asynchronous Triggers

The HAP processes described herein may incorporate the generation of data and/or alerts that are fed into an overall patient healthcare plan (PHP) in the form of synchronous or asynchronous events, patient interaction, healthcare provider interaction, and/or patient healthcare alerts. These features of the PHP are further described in the HEALTHCARE DELIVERY SYSTEM AND METHOD patent application. For example, a database transfer of a BLOOD PRESSURE reading into a particular database field might trigger an asynchronous patient query/response dialog or video presentation to the patient with questions as to their overall health condition and may be associated with a healthcare provider alert if the patient responses are considered indicative of declining health status. Video scripting and/or diverse user interaction contexts (UICs) may be implemented within this PHP framework as described in the VIDEO DATA EXTENSION SYSTEM AND METHOD patent application and the DYNAMIC VIDEO SCRIPTING SYSTEM AND METHOD patent application.

This type of asynchronous triggering may also occur for the HAP in situations where patient medical data is collected in real-time and stored in a patient history database (PHD). This collected data may be from a mobile user device (MUD) and/or a medical instrumentation device (MID) that is selected from (among others) a group consisting of: weight scale; pulse oximeter; blood pressure meter; and blood glucose meter.

This type of asynchronous triggering may also occur for the HAP in situations where patient medical data is accessed from a patient history database (PHD). The mere accessing of this data may trigger activity directed towards other healthcare providers to ensure that data presented to one healthcare provider is presented to other patient physicians to ensure that all of the healthcare professionals are apprised of related patient statistics.

Preferred Embodiment System Summary

The present invention preferred exemplary system embodiment anticipates a wide variety of variations in the basic theme of construction, but can be generalized as a distributed healthcare database system comprising:
(a) data mapping server (DMS);
(b) data request server (DRS);
(c) data service server (DSS); and
(d) computer communication network (CCN);
wherein
the DMS is configured to establish communication with the DRS via the CCN;
the DMS is configured to establish communication with the DSS via the CCN;
the DMS is configured to associate a data access matrix (DAM) with the transfer of data between a database (DRD) controlled by the DRS and a database (DSD) controlled by the DSS;
the DAM is configured to be accessed by indexes associated with individual data item (IDI) datums associated with the DRS and the DSS;
the DAM is configured to associate an access control list (ACL) between the DRS and the DSS that is stored within the DAM and located by the DAM indexes;
the DAM is configured to associate a data transfer between the DRS and the DSS via a data mapping process (DMP) reference stored within the DAM and located by the DAM indexes;
the DMS is configured to transfer data between the DRS and the DSS by activating the DMP referenced within the DAM; and the DMP when activated by the DMS transfers data between the DRS and the DSS using a predefined data transfer mode (DTM) limited by the ACL.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a distributed healthcare database method comprising:

(1) with a data mapping server (DMS), establishing communication with a data request server (DRS) via a computer communication network (CCN);
(2) with the DMS, establishing communication with a data service server (DSS) via the CCN;
(3) with the DMS, associating a data access matrix (DAM) with the transfer of data between a database (DRD) controlled by the DRS and a database (DSD) controlled by the DSS;
(4) with the DMS, configuring the DAM to be accessed by indexes associated with individual data item (IDI) datums associated with the DRS and the DSS;
(5) with the DMS, configuring the DAM to associate an access control list (ACL) between the DRS and the DSS that is stored within the DAM and located by the DAM indexes;
(6) with the DMS, configuring the DAM to associate a data transfer between the DRS and the DSS via a data mapping process (DMP) reference stored within the DAM and located by the DAM indexes;
(7) with the DMS, transferring data between the DRS and the DSS by activating the DMP referenced within the DAM; and
(8) with the DMS, executing the DMP to transfer data between the DRS and the DSS using a predefined data transfer mode (DTM) limited by the ACL.

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the CCN comprises the Internet.
An embodiment wherein the DTM is selected from a group consisting of: read; write; and update.
An embodiment wherein the DAM comprises a healthcare activity process (HAP) that is triggered based on the DTM.
An embodiment wherein the DAM comprises a healthcare activity process (HAP) that is triggered based on the DTM with the DTM selected from a group consisting of: read; write; and update.
An embodiment wherein the DAM comprises a healthcare activity process (HAP) that is triggered on activation of patient data collected from a mobile user device (MUD).
An embodiment wherein the DAM comprises a healthcare activity process (HAP) that is triggered on activation of the DMP when processing data from a medical instrumentation device (MID) that is selected from a group consisting of: weight scale; pulse oximeter; blood pressure meter; and blood glucose meter.
An embodiment wherein the DAM comprises a healthcare activity process (HAP) that is triggered based on the access to data within a patient history database (PHD).
An embodiment wherein the DAM comprises a healthcare activity process (HAP) that is triggered on activation of a data mapping process (DMP) referenced within the DAM, the HAP comprising an asynchronous processing thread within a patient healthcare plan (PHP).
An embodiment wherein the DMS is configured to scan the DAM for alternate data transfers related to servers other than the DRS and the DSS and trigger DMPs associated with the alternate data transfers.
An embodiment wherein the DAM is configured to trigger an alert within a patient healthcare plan (PHP) when the DMP is activated.

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710, 578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method distributing healthcare database access has been disclosed. The system and method interpose a data mapping server (DMS) between a data request user (DRS) and data service user server (DSS) to manage data transfers between the DSS and the DRS such that disparate database characteristics of the DRS/DSS are accommodated in real-time and permit asynchronous healthcare activity to be triggered. The DMS operates with a data access matrix (DAM) having each referenced DRS/DSS intersection pair associated with read/write control processes (RWP) that include read data (RDD) and write data (WRD) processes to permit data access across the disparate DRS/DSS database boundaries. The DAM may have multiple dimensions to accommodate asynchronously activated process threads within an overall patient healthcare plan (PHP) that operate to trigger healthcare provider alarms and other activity associated with the transfer/update of data between the DSS and the DRS.

What is claimed is:

1. A distributed healthcare database system for administering and maintaining healthcare data among distributed systems comprising:
- an information interchange hub connected to a network;
- a requesting healthcare information system;
- a sending healthcare information system;
- a mobile user device; and
- a medical information device selected from one of a weight scale, a pulse oximeter, a blood pressure meter, and a blood glucose meter;
- wherein the requesting healthcare information system, the sending healthcare information system, and the mobile user device communicate with the information interchange hub via the network;
- wherein the medical information device is connected to the mobile user device; and
- wherein:
- the information interchange hub is configured to:
- receive healthcare data from the mobile device;
- contain a data access matrix that associates individual data items contained on the requesting healthcare system with the sending healthcare information system; and
- scan the data access matrix for alternate data transfers related to healthcare information systems other than the requesting healthcare information system and sending healthcare information system, wherein the data access matrix is configured to trigger data mapping processes associated with the alternate data transfers
- the data access matrix is configured to:
- maintain an access control list containing access permissions between the requesting healthcare system, the sending healthcare system, and the mobile device;
- activate a specified data mapping process associated with the requesting healthcare system and the sending healthcare system;
- the specified data mapping process is configured to:
- form a first data bridge allowing data transfer from the sending healthcare system to the requesting healthcare system;
- activate a first data transfer mode limited by the access control list, wherein the first data transfer mode is configured to convert the data from the sending healthcare system data format to the format required by the requesting healthcare system, and wherein the first data transfer mode is configured to activate a first healthcare activity process contained in the data access matrix;
- the first healthcare activity process is configured to trigger an alert in the healthcare information system to activate healthcare personnel if strictures of the first healthcare activity process require direct healthcare provider intervention based on the data transfer;
- a second specified data mapping process is configured to be activated by data transfer from the mobile device, wherein the data mapping process activates a second data transfer mode to form a second data bridge between the mobile device and the associated requesting and sending healthcare systems;
- a second healthcare activity process is configured to be activated by a data transfer from the mobile device, wherein the mobile device is processing data from a connected medical instrumentation device.

2. The distributed healthcare database system of claim 1 wherein the first and the second data transfer mode are selected from a group consisting of: read, write, and update.

3. The distributed healthcare database system of claim 1 wherein the data access matrix comprises a first and second healthcare activity process that are triggered based on the data transfer mode with the data transfer mode selected from a group consisting of: read, write, and update.

4. The distributed healthcare database system of claim 1 wherein the data access matrix comprises a first and second healthcare activity process that are based on the access to data within a patient history database contained on a healthcare system.

5. The distributed healthcare database system of claim 1 wherein the data access matrix comprises a first and second healthcare activity process that are triggered on activation of a data mapping process referenced within the data access matrix, the first and second healthcare activity process comprising asynchronous processing threads within a patient healthcare plan.

6. A method for administering and maintaining healthcare data among distributed systems comprising the steps:
- receiving healthcare data from a mobile device via a network;
- establishing communication with the requesting healthcare information system via the network;
- establishing communication with the sending healthcare information system via the network;
- configuring a data access matrix that associates individual data items contained on the requesting healthcare system with the sending healthcare information system;
- configuring the data access matrix to maintain an access control list containing access permissions between the requesting healthcare system, the sending healthcare system, and the mobile device;
- configuring the data access matrix to activate a first data mapping process associated with the requesting healthcare system and the sending healthcare system;
- executing the first data mapping process to form a data bridge allowing data transfer from the sending healthcare system to the requesting healthcare system;
- executing the first data mapping process to activate a first data transfer mode limited by the access control list, wherein the first data transfer mode is configured to convert the data from the sending healthcare system data format to the format required by the requesting healthcare system;
- executing a first healthcare activity process to trigger an alert in the healthcare information system to activate healthcare personnel if strictures of the first healthcare activity process require direct healthcare provider intervention based on the data transfer;
- executing a second data mapping process activated by data transfer from the mobile device, wherein the interchange hub executes a second data mapping process to activate a second data transfer mode, wherein the second data transfer mode forms a second data bridge between the mobile device and the associated requesting and sending healthcare systems;

executing a second healthcare activity process activated by a data transfer from a mobile device, wherein the mobile device is processing data from a connected medical instrumentation device, wherein the medical instrumentation device is selected from a group consisting of: weight scale, pulse oximeter, blood pressure meter, and blood glucose meter; and scanning the data access matrix for alternate data transfers related to healthcare information systems other than the requesting healthcare information system and sending healthcare information system, wherein the interchange hub configures the data access matrix to trigger data mapping processes associated with the alternate data transfers.

7. The method of claim 6 wherein the first and second data transfer modes are selected from a group consisting of: read, write, and update.

8. The method of claim 6 wherein the data access matrix comprises a first and second healthcare activity process that are triggered based on the first and second data transfer mode with the first and second data transfer mode selected from a group consisting of: read, write, and update.

9. The method of claim 6 wherein the data access matrix comprises a first and second healthcare activity process that are triggered based on the access to data within a patient history database contained on a healthcare system.

10. The method of claim 6 wherein the data access matrix comprises a first and second healthcare activity process that is triggered on activation of a data mapping process referenced within the data access matrix the first and second healthcare activity process comprising an asynchronous processing thread within a patient healthcare plan.

11. A tangible non-transitory computer usable medium having computer-readable code means embodied thereon comprising a method for administering and maintaining healthcare data among distributed systems comprising the steps:

receiving healthcare data from a mobile device via a network;

establishing communication with the requesting healthcare information system via the network;

establishing communication with the sending healthcare information system via the network;

configuring a data access matrix that associates individual data items contained on the requesting healthcare system with the sending healthcare information system;

configuring the data access matrix to maintain an access control list containing access permissions between the requesting healthcare system, the sending healthcare system, and the mobile device;

configuring the data access matrix to activate a first data mapping process associated with the requesting healthcare system and the sending healthcare system;

executing the first data mapping process to form a data bridge allowing data transfer from the sending healthcare system to the healthcare system;

executing the first data mapping process to activate a first data transfer mode limited by the access control list, wherein the first data transfer mode is configured to convert the data from the sending healthcare system data format to the format required by the requesting healthcare system;

executing a first healthcare activity process to trigger an alert in the healthcare information system to activate healthcare personnel if strictures of the first healthcare activity process require direct healthcare provider intervention based on the data transfer;

executing a second data mapping process activated by data transfer from the mobile device, wherein the interchange hub executes a second data mapping process to activate a second data transfer mode, wherein the second data transfer mode forms a second data bridge between the mobile device and the associated requesting and sending healthcare systems;

executing a second healthcare activity process activated by a data transfer from mobile device, wherein the mobile device is processing data from a connected medical instrumentation device, wherein the medical instrumentation device is selected from a group consisting of: weight scale, pulse oximeter, blood pressure meter, and blood glucose meter; and scanning the data access matrix for alternate data transfers related to healthcare information systems other than the requesting healthcare information system and sending healthcare information system, wherein the interchange hub configures the data access matrix to trigger data mapping processes associated with the alternate data transfers.

12. The tangible non-transitory computer usable medium of claim 11 wherein the first and second data transfer modes are selected from a group consisting of: read, write, and update.

13. The tangible non-transitory computer usable medium of claim 11 wherein the data access matrix comprises a first and second healthcare activity process that are triggered based on the first and second data transfer modes with the first and second data transfer modes selected from a group consisting of: read, write, and update.

14. The tangible non-transitory computer usable medium of claim 11 wherein the data access matrix comprises a first and second healthcare activity process that are triggered based on the access to data within a patient history database contained on a healthcare system.

15. The tangible non-transitory computer usable medium of claim 11 wherein the data access matrix comprises a first and second healthcare activity process that are triggered on activation of a data mapping process referenced within the data access matrix, the first and second healthcare activity process comprising an asynchronous processing thread within a patient healthcare plan.

* * * * *